(12) United States Patent (10) Patent No.: US 12,636,478 B2
Haslam et al. (45) Date of Patent: May 26, 2026

(54) HEMOSTASIS VALVE DEVICE

(71) Applicants: Merit Medical Systems, Inc., South Jordan, UT (US); Icahn School of Medicine at Mount Sinai, New York, NY (US)

(72) Inventors: Michael Dean Haslam, Sandy, UT (US); Jim Mottola, West Jordan, UT (US); Benjamin Rapoport, New York, NY (US); Thomas J. Oxley, New York, NY (US); Alexis Bruhat, New York, NY (US)

(73) Assignees: Merit Medical Systems, Inc., South Jordan, UT (US); Icahn School of Medicine @ Mount Sinai, New York, NY (US)

( * ) Notice: Subject to any disclaimer, the term of this patent is extended or adjusted under 35 U.S.C. 154(b) by 599 days.

(21) Appl. No.: 17/644,234

(22) Filed: Dec. 14, 2021

(65) Prior Publication Data

US 2022/0184367 A1 Jun. 16, 2022

Related U.S. Application Data

(60) Provisional application No. 63/124,996, filed on Dec. 14, 2020.

(51) Int. Cl.
A61M 39/06 (2006.01)
(52) U.S. Cl.
CPC ... A61M 39/0613 (2013.01); A61M 2039/062 (2013.01); A61M 2039/0673 (2013.01)

(58) Field of Classification Search
CPC ...... A61M 39/0613; A61M 2039/0673; A61M 2039/062; A61M 39/06;
(Continued)

(56) References Cited

U.S. PATENT DOCUMENTS

| | | | |
|---|---|---|---|
| 4,723,550 A | 2/1988 | Bales et al. | |
| 4,857,062 A | 8/1989 | Russell | |

(Continued)

FOREIGN PATENT DOCUMENTS

| | | | |
|---|---|---|---|
| JP | 6249789 B2 | 12/2017 | |
| WO | 9945983 A1 | 9/1999 | |

OTHER PUBLICATIONS

International Search Report and Written Opinion dated Mar. 21, 2022 for PCT/US2021/063103.

(Continued)

*Primary Examiner* — Michael J Tsai
*Assistant Examiner* — Kathleen Paige Farrell
(74) *Attorney, Agent, or Firm* — Dorsey & Whitney LLP

(57) ABSTRACT
Hemostasis valve devices and methods of use are disclosed. The hemostasis valve devices include a body member, a slide member, an introducer member, a valve cap, and a valve member. The body member and slide member can be gripped by a user's finger and thumb, respectively. The slide member can be distally displaced by the user's thumb to distally displace the introducer member through the valve member to open the valve member to allow passage of a medical appliance through the valve member. The introducer member can be selectively locked in a distal position to keep the valve open.

20 Claims, 17 Drawing Sheets

(58) Field of Classification Search
CPC .... A61M 2025/09116; A61M 39/0693; A61M 2039/0633; A61M 39/10; A61M 39/0606; A61M 39/1011; A61M 2039/1027; A61M 39/20; A61M 2039/064
See application file for complete search history.

(56)                    References Cited

U.S. PATENT DOCUMENTS

| | | | |
|---|---|---|---|
| 4,925,450 A | 5/1990 | Imonti et al. | |
| 4,978,341 A | 12/1990 | Niederhauser | |
| 5,030,206 A | 7/1991 | Lander | |
| 5,059,186 A | 10/1991 | Yamamoto et al. | |
| 5,078,688 A | 1/1992 | Lobodzinski et al. | |
| 5,125,915 A * | 6/1992 | Berry ................ | A61M 39/0613 604/533 |
| 5,135,492 A | 8/1992 | Melker et al. | |
| 5,195,980 A | 3/1993 | Catlin | |
| 5,203,774 A | 4/1993 | Gilson et al. | |
| 5,224,929 A | 7/1993 | Remiszewski | |
| 5,269,764 A | 12/1993 | Vetter et al. | |
| 5,269,771 A | 12/1993 | Thomas et al. | |
| 5,273,546 A | 12/1993 | McLaughlin et al. | |
| 5,324,271 A | 6/1994 | Abiuso et al. | |
| 5,338,313 A | 8/1994 | Mollenauer et al. | |
| 5,350,363 A | 9/1994 | Goode et al. | |
| 5,350,364 A | 9/1994 | Stephens et al. | |
| 5,356,394 A | 10/1994 | Farley et al. | |
| 5,364,371 A | 11/1994 | Kamen | |
| 5,382,230 A | 1/1995 | Bonn | |
| 5,395,349 A | 3/1995 | Quiachon et al. | |
| 5,514,109 A | 5/1996 | Mollenauer et al. | |
| 5,542,933 A | 8/1996 | Marks | |
| 5,562,611 A | 10/1996 | Transue | |
| 5,569,208 A | 10/1996 | Woelpper et al. | |
| 5,575,767 A | 11/1996 | Stevens | |
| 5,584,314 A | 12/1996 | Bron | |
| 5,590,327 A | 12/1996 | Biliris et al. | |
| 5,591,137 A | 1/1997 | Stevens | |
| 5,693,025 A | 12/1997 | Stevens | |
| 5,911,710 A | 6/1999 | Barry et al. | |
| 5,921,968 A | 7/1999 | Lampropoulos et al. | |
| 5,935,112 A | 8/1999 | Stevens et al. | |
| 6,287,280 B1 | 9/2001 | Lampropoulos et al. | |
| 6,331,176 B1 | 12/2001 | Becker et al. | |
| 6,458,103 B1 | 10/2002 | Albert et al. | |
| 6,572,590 B1 * | 6/2003 | Stevens ............. | A61M 39/0613 |
| 6,695,818 B2 | 2/2004 | Wollschlager | |
| 6,986,749 B2 | 1/2006 | Wollschlager | |
| 2002/0002352 A1 | 1/2002 | Becker et al. | |
| 2005/0085789 A1 | 4/2005 | Khan et al. | |
| 2007/0010796 A1 | 1/2007 | Moran et al. | |
| 2007/0106262 A1 | 5/2007 | Becker et al. | |
| 2007/0112355 A1 | 5/2007 | Salahieh et al. | |
| 2009/0192579 A1 * | 7/2009 | Ransbury .......... | A61M 39/0613 607/119 |
| 2009/0259200 A1 * | 10/2009 | Lampropoulos .. | A61M 39/0613 604/249 |
| 2009/0281525 A1 | 11/2009 | Harding et al. | |
| 2013/0199947 A1 * | 8/2013 | Tennican .............. | A61M 39/20 206/216 |
| 2018/0256874 A1 * | 9/2018 | Agrawal .......... | A61M 39/0693 |
| 2018/0296221 A1 | 10/2018 | Jiang et al. | |
| 2018/0344981 A1 * | 12/2018 | Laduca .................. | A61L 29/06 |
| 2019/0070401 A1 | 3/2019 | Merritt et al. | |
| 2019/0282741 A1 * | 9/2019 | Franano .............. | A61M 60/816 |
| 2020/0147360 A1 * | 5/2020 | Arnett .............. | A61M 25/0662 |

OTHER PUBLICATIONS

European Search Report dated Nov. 20, 2024 for EP21908022.3.
European Search Report dated Oct. 10, 2024 for EP21907562.9.
Office Action dated Dec. 29, 2025 for U.S. Appl. No. 18/333,337.

* cited by examiner

HEMOSTASIS VALVE DEVICE

RELATED APPLICATIONS

This application claims priority to U.S. Provisional Application No. 63/124,996, filed on Dec. 14, 2020 and titled, "Hemostasis Valve Device," which is hereby incorporated by reference in its entirety.

TECHNICAL FIELD

The present disclosure relates generally to medical devices. More specifically, the present disclosure relates to medical devices used to access a patient's vascular system. More specifically, the present disclosure relates to medical devices used to control blood leakage while accessing the patient's vascular system.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

14A is a cross-sectional view of another embodiment of a hemostasis valve device in a ready state.

Figure 14A:
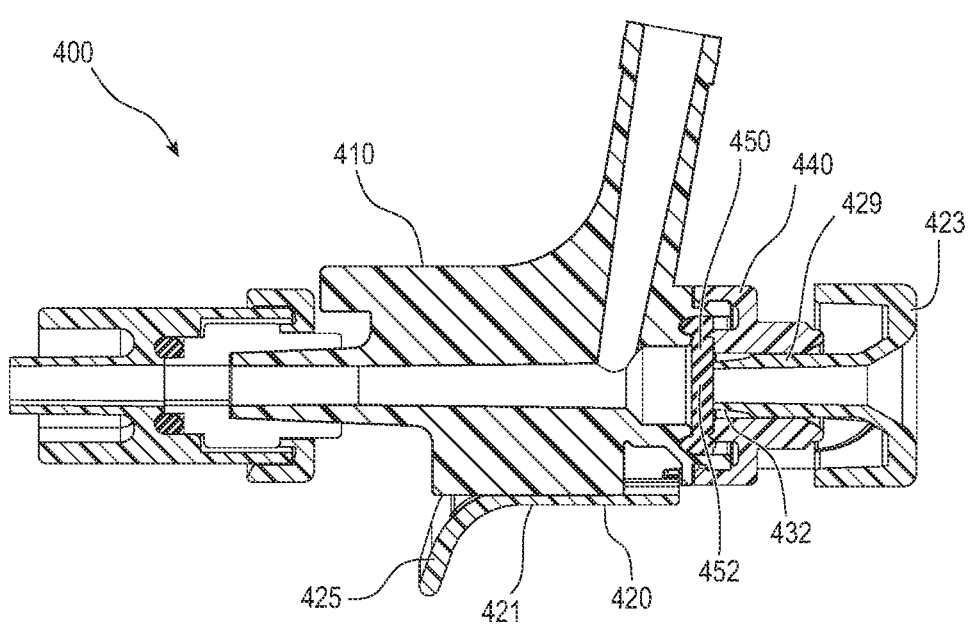
Figure 14B:
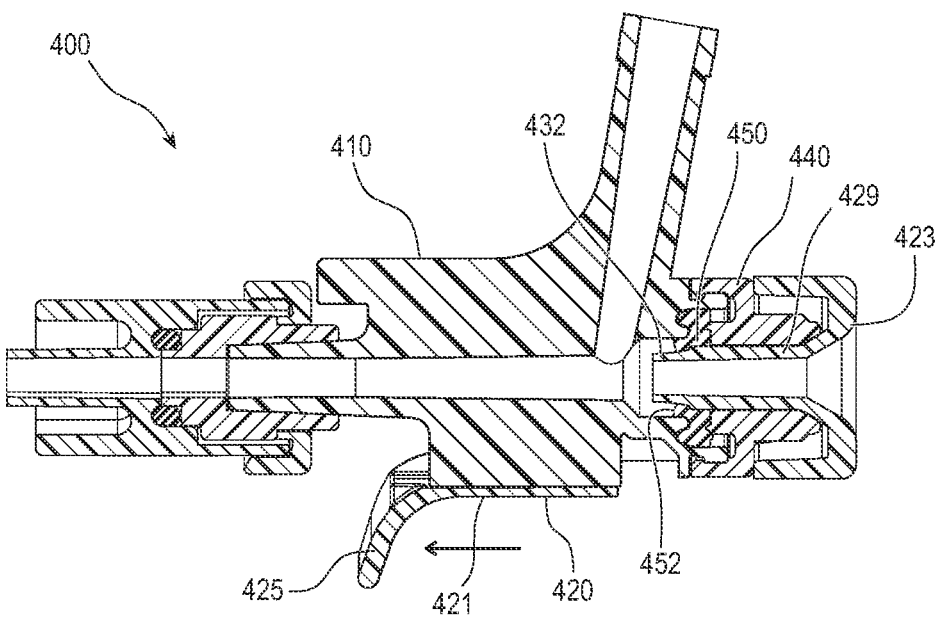

FIG. 14B is a cross-sectional view of the hemostasis valve device of FIG. 14A in a valve open state.

DETAILED DESCRIPTION

In certain instances, hemostasis valve devices are used to prevent blood leakage and to maintain a position of a medical appliance while accessing a patient's vascular system to treat a patient. For example, treatment of the patient's brain, heart, kidneys, liver, and lungs may be accomplished from an intravascular approach. A catheter may be inserted into the vascular system to provide access to an area of treatment. A hemostasis valve device can be coupled to a proximal end of the catheter. The hemostasis valve device can prevent leakage of blood from the catheter and hold medical appliances, such as a guidewire, that are inserted through the hemostasis valve device into the catheter in a desired position Embodiments herein describe hemostasis valve devices and methods of use thereof. The hemostasis valve devices can be coupled to a catheter inserted into a patient's vascular system for treatment of the patient's brain or other treatment site. In some embodiments within the scope of this disclosure, the hemostasis valve devices include a body member having a side-arm and a finger grip portion, a slide member having a thumb grip portion and a cap, an introducer member coupled to the slide member or actuator, a valve cap coupled to the body member, and a valve member disposed between the valve cap and the body member. The introducer member can be distally displaced by the slide member to a first distal position where the introducer member passes through the valve member to open the valve member and to a second distal position where the introducer member is locked in the second distal position to keep the valve member open. A medical appliance can be passed through the introducer member into the catheter when the introducer member is in the first and second distal positions. When desired, the introducer member can be unlocked from the second distal position and return to a proximal position. In the proximal position, the introducer member does not pass through the valve member and the valve member is closed to prevent blood leakage and to hold the medical appliance in a desired position. When the introducer member is displaced to the first distal position, the second distal position, and the proximal position, it is rotated about a longitudinal axis of the introducer member.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Figure 12:
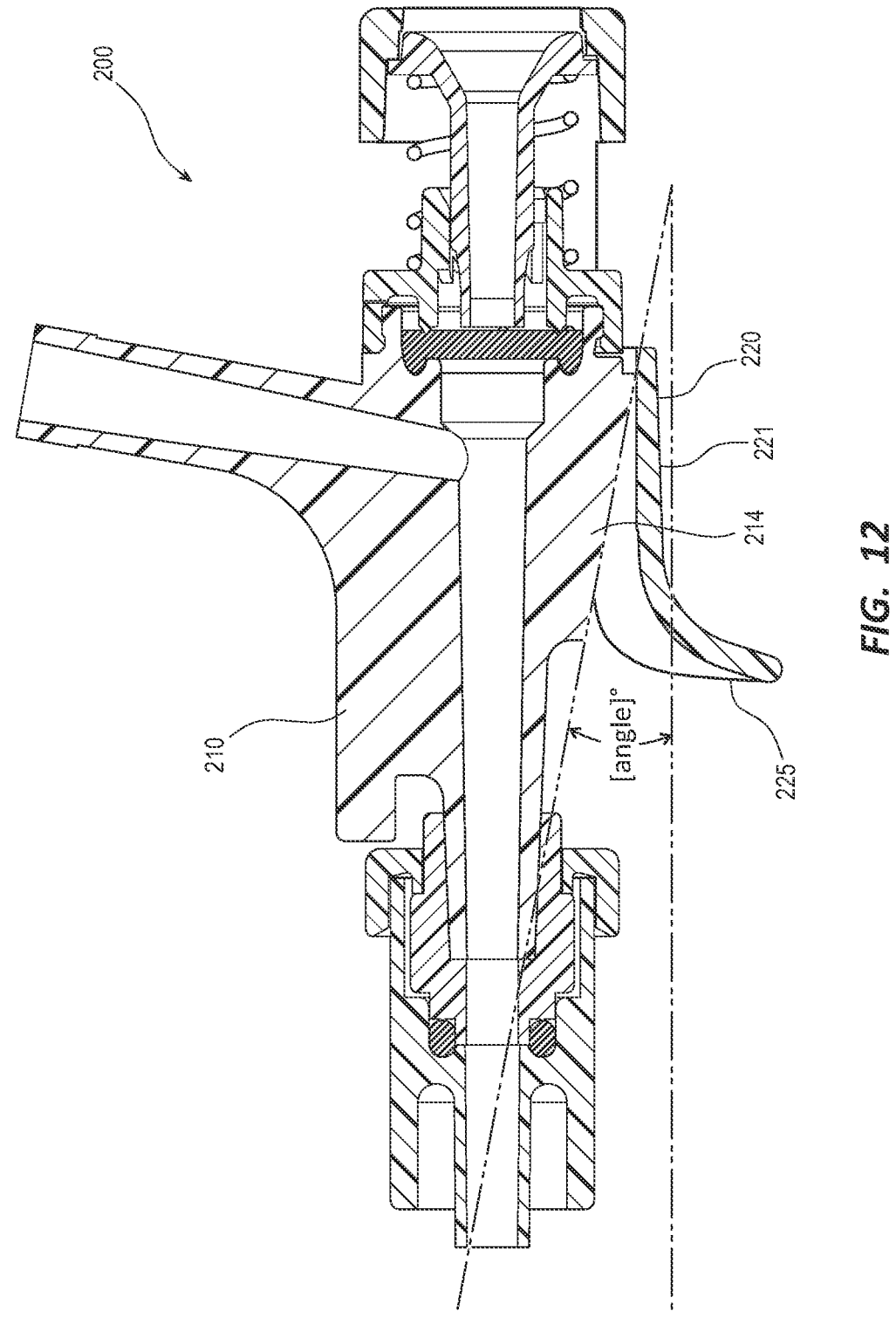
FIG. 12 is a side cross-sectional view of another embodiment of a hemostasis valve device having an inclined rail.
Figure 13A:
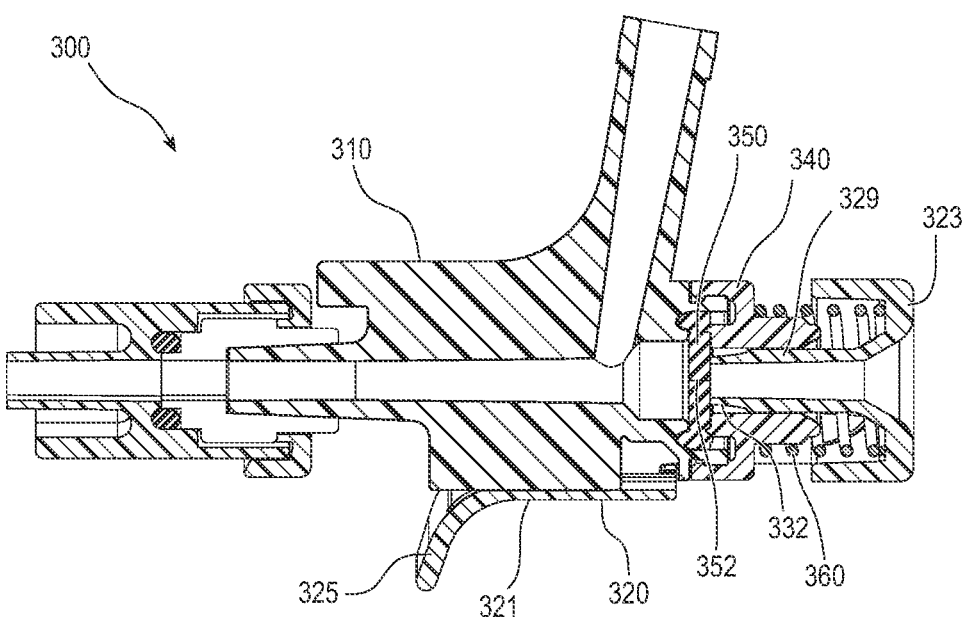
FIG. 13A is a cross-sectional view of another embodiment of a hemostasis valve device in a ready state.
Figure 13B:
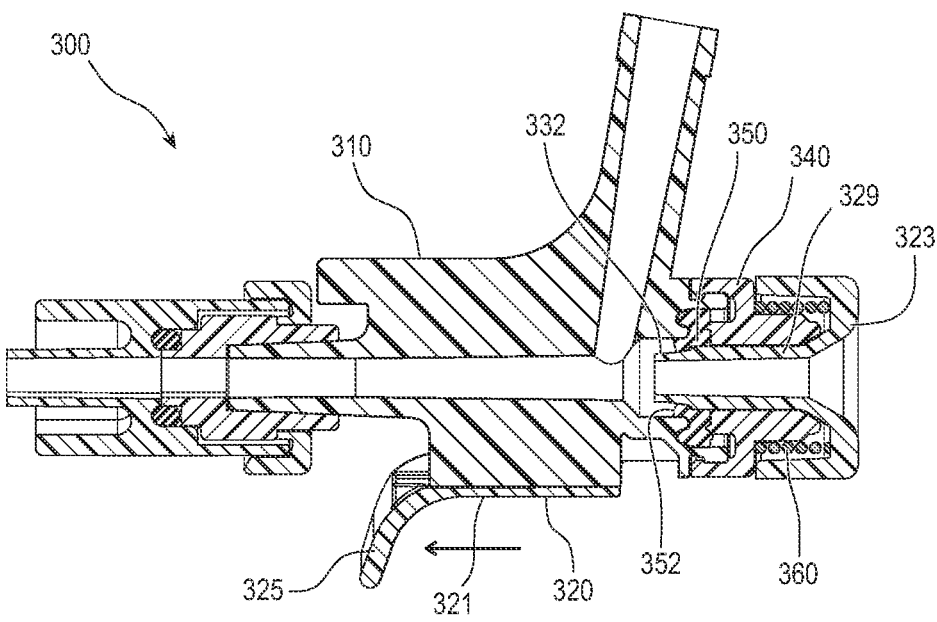
FIG. 13B is a cross-sectional view of the hemostasis valve device of FIG. 13A in an open state.

FIGS. 1-11B illustrate an embodiment of a hemostasis valve device. FIG. 12 illustrates another embodiment of a hemostasis valve device. FIGS. 13A and 13B illustrate yet another embodiment of a hemostasis valve device. FIGS. 14A and 14B illustrate yet another embodiment of a hemostasis valve device. In certain views each device may be coupled to, or shown with, additional components not included in every view. Further, in some views only selected components are illustrated, to provide detail into the relationship of the components. Some components may be shown in multiple views but not discussed in connection with every view. Disclosure provided in connection with any figure is relevant and applicable to disclosure provided in connection with any other figure or embodiment.

Figure 1:
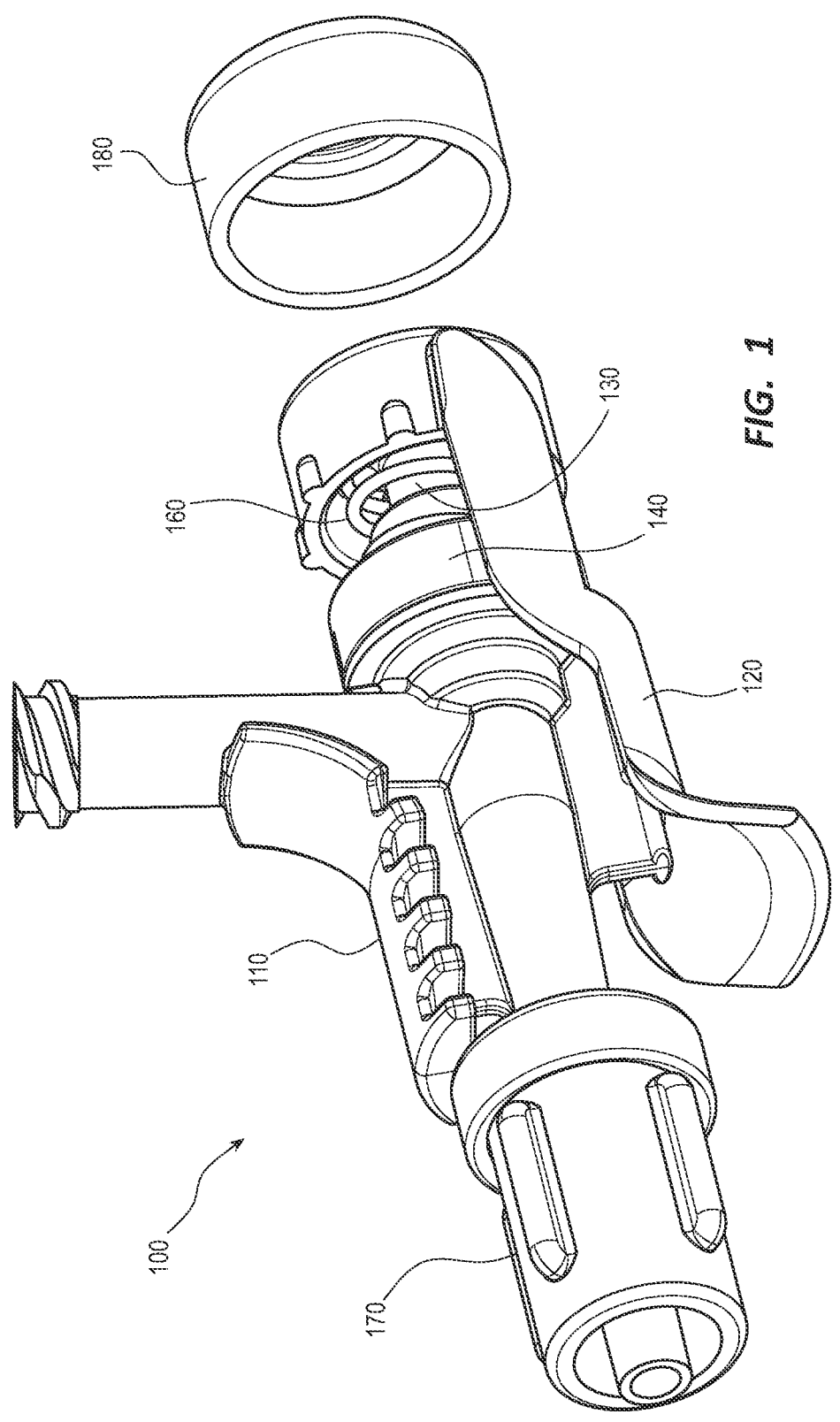
FIG. 1 is a perspective view of an embodiment of a hemostasis valve device.

FIGS. 1-3 illustrate a hemostasis valve device 100. As illustrated, the depicted embodiment includes a body member 110, a slide member 120, an introducer member 130, a valve cap 140, a valve member 150, a resilient member 160, and a fluid fitting 170. The valve cap 140 is fixedly coupled to the body member 110 with the valve member 150 sealingly disposed between the body member 110 and the valve cap 140. The introducer member 130 is slidingly coupled to and disposed through the valve cap 140 such that a proximal portion of the introducer member 130 extends proximally from the valve cap 140. The slide member 120 is slidingly coupled to the body member 110 and operably coupled to the introducer member 130 wherein the slide member 120 can distally displace the introducer member 130. The resilient member 160 is disposed between the introducer member 130 and the valve cap 140 and configured to apply a proximally directed force to the introducer member 130. The fluid fitting 170 is coupled to a distal end and in fluid communication with the body member 110. The body member 110 can be formed of any suitable translucent or transparent material, such as polycarbonate, acrylic, polypropylene, nylon, copolyester, etc. In some embodiments, a length of the hemostasis valve 100 is between 4 centimeters and 8 centimeters, including between 4 centimeters and 6 centimeters.

FIGS. 2A-2B and 3A-3B illustrate the body member 110. As illustrated, the depicted embodiment includes a body bore 111, a side-arm 112, a finger grip portion 113, and a guide rail 114. The body bore 111 extends from a proximal end to a distal end of the body member 110. The body bore 111 includes a valve portion 118 disposed at a proximal end of the body member 110 and proximal to the side-arm 112. The valve portion 118 may be configured to receive the valve member 150 to seal the valve portion 118 of the body bore 111 to prevent blood and/or fluid from leaking from the body bore 111. The side-arm 112 extends radially outward from the body member 110 at an angle ranging from about 60 degrees to about 90 degrees and may be about 80 degrees relative to a longitudinal axis of the body member 110. The side-arm 112 includes a side-arm bore 115 extending therethrough. The side-arm bore 115 is in fluid communication with the body bore 111. The side-arm 112 may include a fluid fitting (e.g., a female Luer slip or female Luer lock fitting) disposed at a proximal end configured to be coupled to a mating fitting (e.g., male Luer slip or male Luer lock fitting) of a medical device.

The finger grip portion 113 is disposed distal to and coupled to the side-arm 112. The finger grip portion 113 includes an elongate arcuate surface 116 configured for gripping by a user's finger. In other embodiments, the finger grip portion 113 may include grip enhancing features, such as bumps, recesses, grooves, ridges, pliable over-molded material, etc. A proximal portion of the finger grip portion 113 includes a finger tab 117 having an arcuate shape. The finger tab 117 can receive the user's finger to prevent distal movement of the hemostasis valve device 100 when in use. The guide rail 114 is disposed circumferentially opposite of the finger grip portion 113. The guide rail 114 extends radially outward from and parallel to the longitudinal axis of the body member 110. The guide rail 114 may include a T-shape configured to engage with the slide member 120.

FIGS. 2A-2B and 4A-4B illustrate the slide member 120. As illustrated the depicted embodiment includes a thumb grip portion 121, a cap portion 123, and a linking portion 126. The thumb grip portion 121 extends distally from the linking portion 126. The thumb grip portion 121 includes an elongate arcuate surface configured for gripping by a user's thumb. In other embodiments, the thumb grip portion 121 may include grip enhancing features, such as bumps, recesses, grooves, ridges, pliable over-molded material, etc. A thumb tab 125 is disposed at a distal end of the thumb grip portion 121 and includes an arcuate shape that extends radially outward from the thumb grip portion 121. The thumb tab 125 can receive the user's finger to facilitate distal movement of the slide member 120 when the hemostasis valve device 100 is in use. In other embodiments, the thumb tab 125 may include any suitable shape to receive the user's thumb to facilitate distal movement of the slide member 120. For example, the thumb tab 125 may extend radially outward at a right angle or any other angle relative to the thumb grip portion 121.

A guide slot 122 is disposed on an inner surface of the thumb grip portion 121. The guide slot 122 extends parallel to a longitudinal axis of the thumb grip portion 121. The guide slot 122 may include a T-shape slot with undercuts configured to slidingly receive the guide rail 114 of the body member 110.

The cap portion 123 is coupled to a proximal end of the linking portion 126. The cap portion 123 includes a cap opening 127 for passage of medical appliances into the hemostasis valve device 100 and internal, distally directed cap teeth 124 that operably engage with the introducer member 130 to rotate the introducer member 130. The number of cap teeth 124 may be one, two, three, four, or more. The linking portion 126 is disposed between the thumb grip portion 121 and the cap portion 123. The linking member 126 can include two side rails 128 with top and bottom openings disposed between the side rails 128. The slide member 120 can be formed from any suitable rigid transparent or translucent material, such as polycarbonate, acrylic, acrylonitrile butadiene styrene, polypropylene, high density polyethylene, polyoxymethylene, nylon, copolyester, etc.

FIGS. 2A-2B and 5A-5B illustrate the introducer member 130. As illustrated, the depicted embodiment includes an introducer bore 131, a nose portion 132, a head portion 133, and a body portion 135. The introducer bore 131 extends through the introducer member 130. A proximal portion of the introducer bore 131 can include a funnel shape to facilitate passage of the medical appliances into the introducer bore 131. The nose portion 132 is disposed at a distal end of the introducer member 130. The nose portion 132 can be distally inwardly tapered such that a diameter of a distal end of the nose portion 132 is smaller than a diameter of a proximal end of the nose portion 132.

The head portion 133 includes external, proximally directed head teeth 134. The head teeth 134 can be configured to operably engage with the cap teeth 124 to rotate the introducer member 130 about its longitudinal axis when the hemostasis valve device 100 is in use. The number of head teeth 134 may be one, two, three, four, five, or more. The body portion 135 is disposed between the nose portion 132 and the head portion 133. A diameter of the body portion 135 is smaller than a diameter of the head portion 133. A guide member 136 extends radially outward from the body portion 135. The guide member 136 may include a distally tapered proximal surface. The introducer member 130 may include one, two, three, four, or more guide members 136. The introducer member 130 can be formed from any suitable rigid transparent or translucent material, such as polycarbonate, acrylic, polycarbonate, acrylic, acrylonitrile butadiene styrene, polypropylene, high density polyethylene, polyoxymethylene, nylon, copolyester, etc.

FIGS. 2A-2B and 6A-6B illustrate the valve cap 140. As illustrated in the depicted embodiment, the valve cap 140 includes a proximal portion 143 and a distal portion 144. The proximal portion 143 has a diameter smaller than a diameter of the distal portion 144. A guide channel 141 is disposed on an inner surface of the proximal portion 143. The guide channel 141 extends parallel to a longitudinal axis of the valve cap 140. The number of guide channels 141 can be one, two, three, four, or more. The guide channel 141 is sized to slidingly receive the guide member 136. A lock member 142 is disposed on the inner surface of the proximal portion 143 between adjacent guide channels 141. The number of lock members 142 may be one, two, three, four, or more. The lock member 142 includes a distally tapered proximal surface 147 configured to engage with the distally tapered proximal surface of the guide member 136 when the introducer member 130 is in a second distal position. The lock member 142 also includes a distally tapered distal surface 148 configured to engage with the distally tapered proximal surface of the guide member 136 when the introducer member 130 is transitioned from the second distal position to a proximal position.

The distal portion 144 includes a snap ring 146 configured to be snapped onto the proximal end of the body member 110 to couple the valve cap 140 to the body member 110 and to retain the valve member 150 between the body member 110 and the valve cap 140. An anti-rotation slot 145 is disposed through the snap ring 146. The anti-rotation slot 145 can engage with the anti-rotation rib 119 to prevent rotation of the cap member 140 relative to the body member 110. The cap member 140 can be formed from any suitable rigid material such as polycarbonate, acrylic, acrylonitrile butadiene styrene, polypropylene, high density polyethylene, polyoxymethylene, nylon, copolyester, etc. In some embodiments, the cap member 140 may comprise a transparent or translucent material.

Figures 2A, 2B:
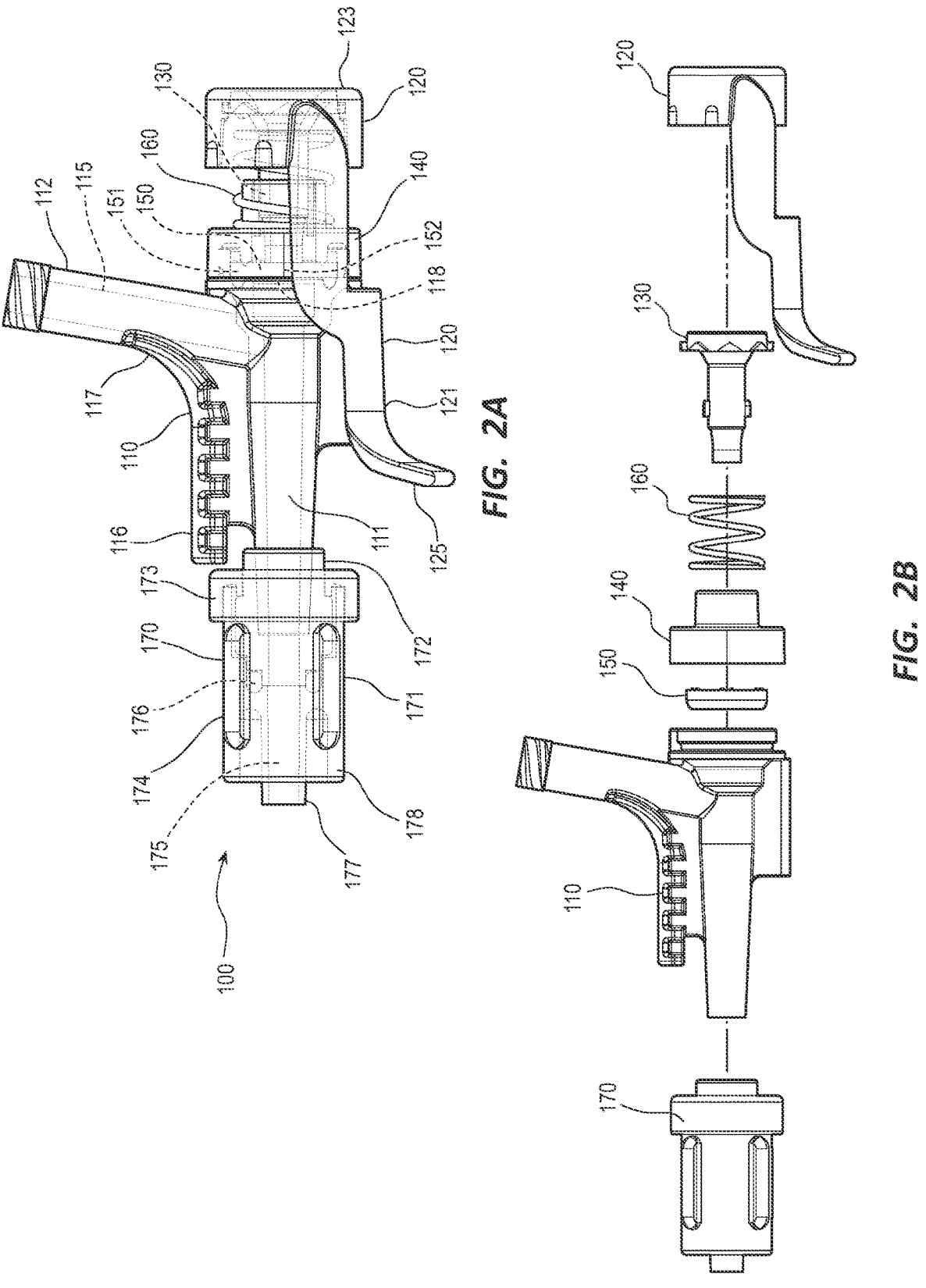
FIG. 2A is a side view of the hemostasis valve device of FIG. 1.
FIG. 2B is an exploded side view of the hemostasis device of FIG. 1
Figure 3A:
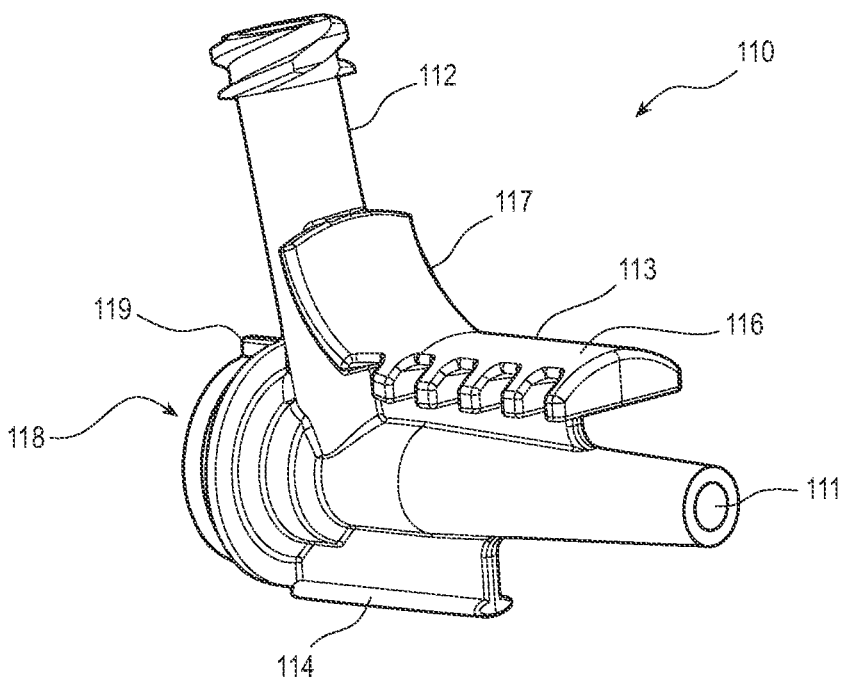
FIG. 3A is a perspective view of an embodiment of a body member of the hemostasis valve device of FIG. 1.
Figure 3B:
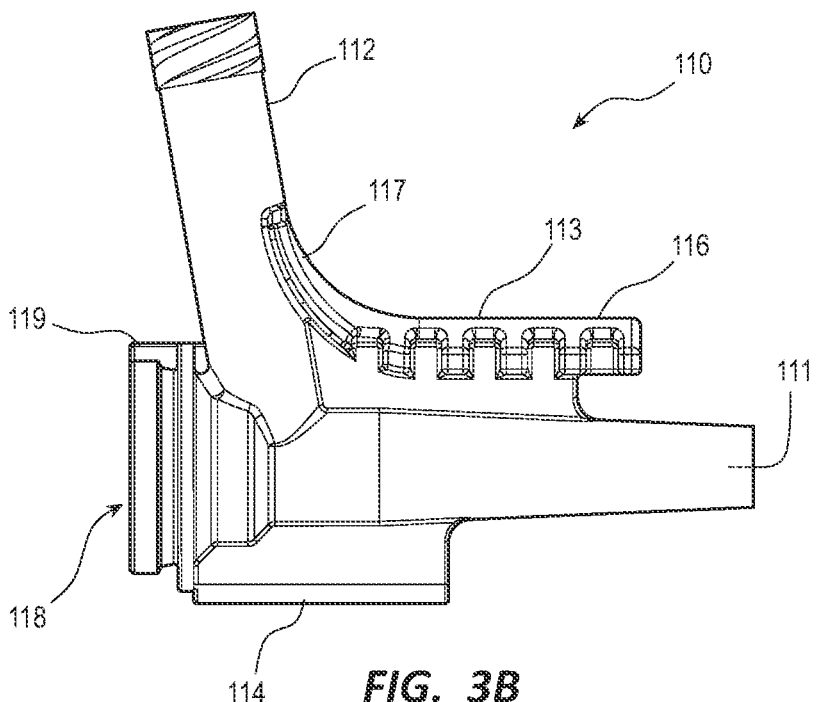
FIG. 3B is a side view of the body member of FIG. 3A.
Figure 4A:
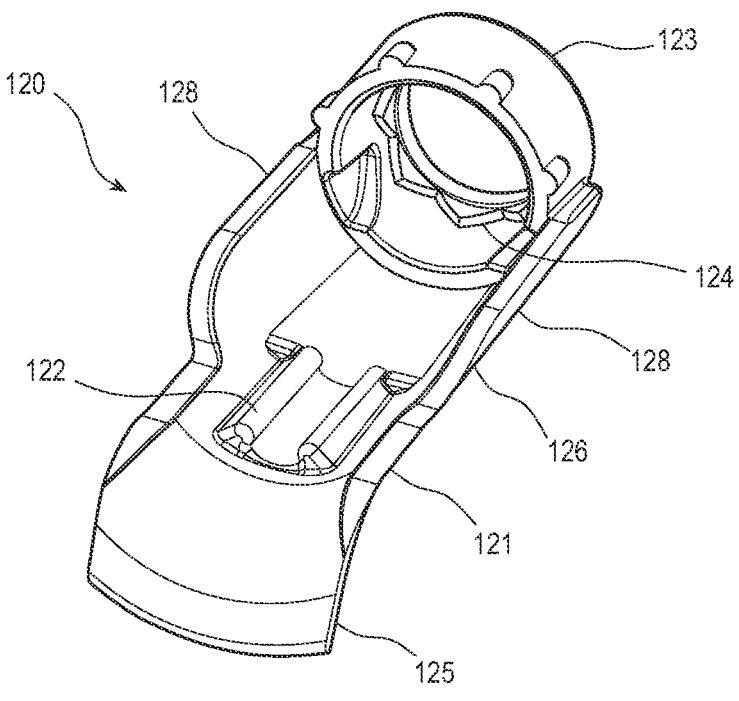
FIG. 4A is a perspective view of an embodiment of a slide member of the hemostasis valve device of FIG. 1.
Figure 4B:
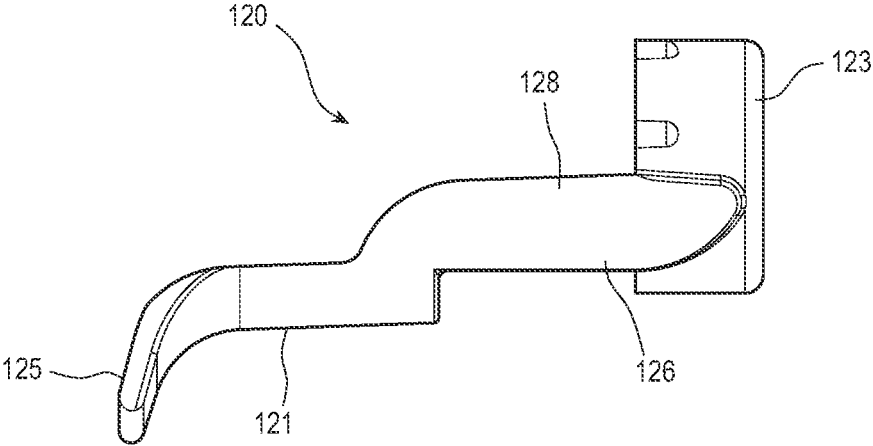
FIG. 4B is a side view of the slide member of FIG. 4A.
Figure 5A:
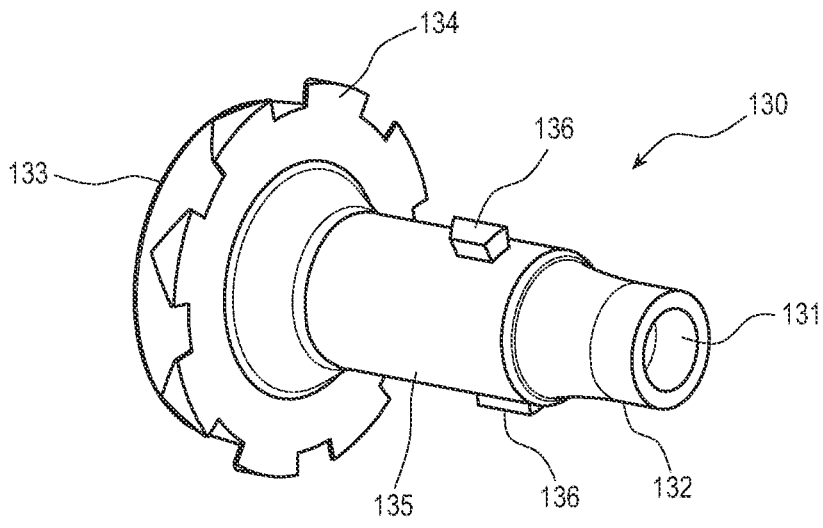
FIG. 5A is a perspective view from a distal end of an embodiment of an introducer member of the hemostasis valve device of FIG. 1.
Figure 5B:
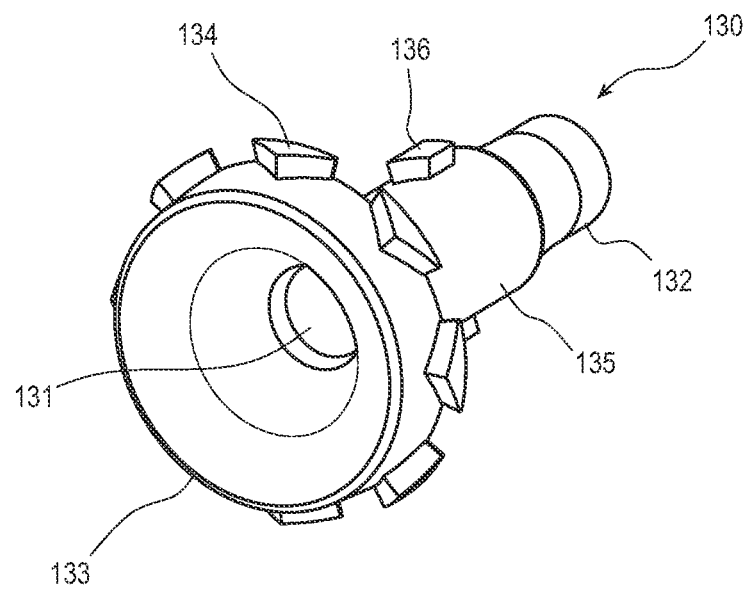
FIG. 5B is a perspective view from a proximal end of the introducer member of FIG. 5A.
Figure 6A:
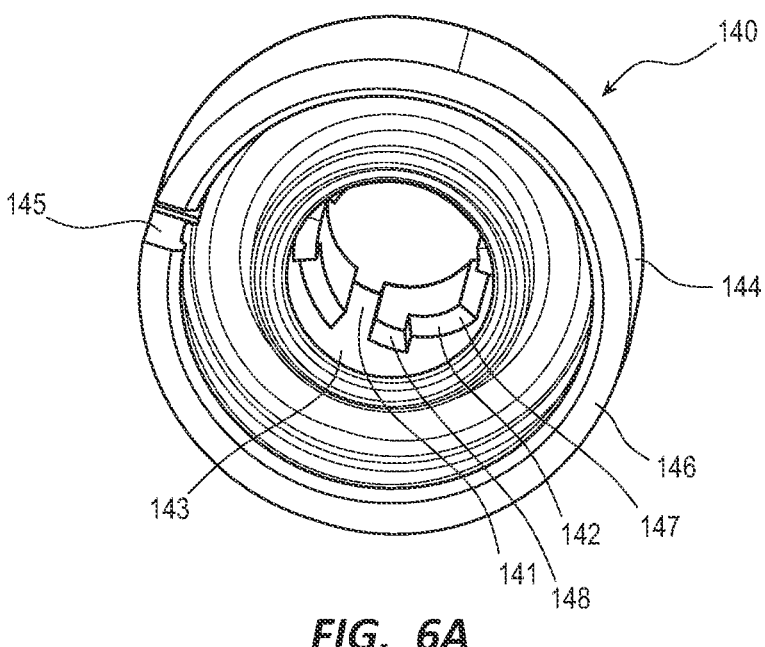
FIG. 6A is a perspective view from a distal end of an embodiment of a valve cap of the hemostasis valve device of FIG. 1.
Figure 6B:
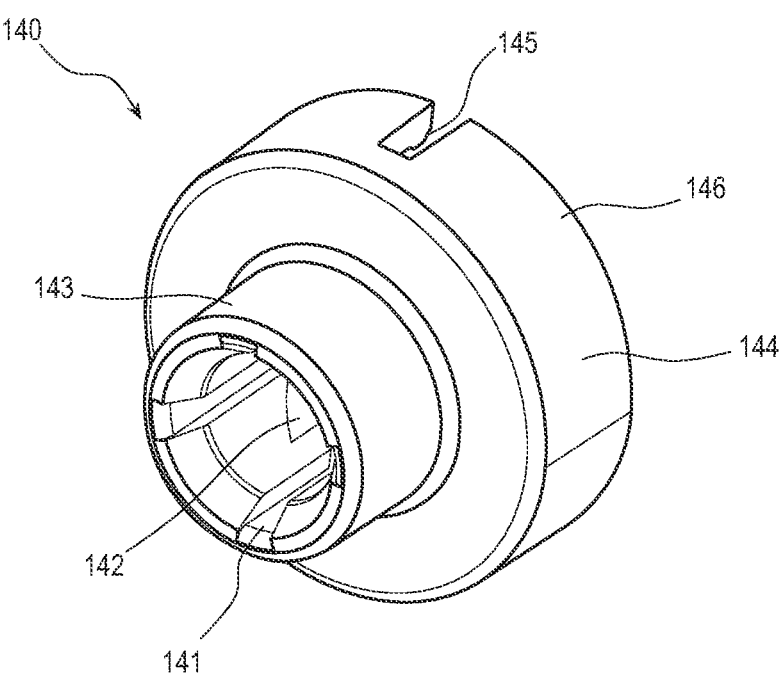
FIG. 6B is a perspective view from a proximal end of the valve cap of FIG. 6A.

FIGS. 2A-2B illustrate the valve member 150 disposed between the body member 110 and the valve cap 140. As depicted in the illustrated embodiment, the valve member 150 includes a disk shape having a thickened circumferential ring 151 to facilitate sealing and retention of the valve member 150 between the body member 110 and the valve cap 140. A slit 152 is disposed in a central portion of the valve member 150. The slit 152 may allow passage of the nose portion 132 of the introducer member 130 through the valve member 150 to open the valve member 150. The valve member 150 may be formed of any suitable elastomeric material, such as silicone rubber, rubber, neoprene, thermoplastic elastomer, polyisoprene, polyurethane, etc.

FIGS. 2A-2B illustrate the resilient member 160 disposed between the head portion 133 of the introducer member 130 and the distal portion 144 of the valve cap 140. In the depicted embodiment of FIGS. 2A-2B, the resilient member 160 is a compression spring configured to apply a proximally directed force to the introducer member 130. In other embodiments, the resilient member 160 may be of any suitable configuration to apply the proximally directed force to the introducer member 130. For example, the resilient member 160 may be an elastomeric cylinder.

FIGS. 2A-2B illustrate the fluid fitting 170 coupled to the distal end of the body member 110. In some embodiments the fluid fitting 170 can include a male Luer lock fitting. In the depicted embodiment of FIG. 2A, the fluid fitting 170 includes a swivel fitting 171. The swivel fitting 171 includes a rotator hub 172, a rotator collar 173, a rotator body 174, and an O-ring 176. The rotator hub 172 is fixedly coupled to the distal end of the body member 110. The rotator collar 173 is rotatably coupled to the rotator hub 172. The rotator body 174 is fixedly coupled to the rotator collar 173 to allow the rotator body 174 to rotate relative to the body member 110. A rotator bore 175 extends through the rotator hub 172 and the rotator body 174 and is in fluid communication with the body bore 111. The O-ring 176 is disposed between the rotator hub 172 and the rotator body 174 and configured to seal the rotator bore 175 when the rotator body 174 is rotated. The rotator body 174 can include a male Luer fitting 177 and a threaded nut 178 configured to couple with a female Luer fitting of a medical appliance, such as a catheter. The swivel fitting 171 can allow the body member 110 to be rotated relative to the catheter without rotation of the catheter or vice versa. In some embodiments, the swivel fitting 171 may allow rotation of the hemostasis valve device 100 to translate into rotation of catheter to facilitate manipulation of the catheter and to allow placement of the hemostasis valve device 100 on a flat surface without rotation of the catheter.

Figure 7:
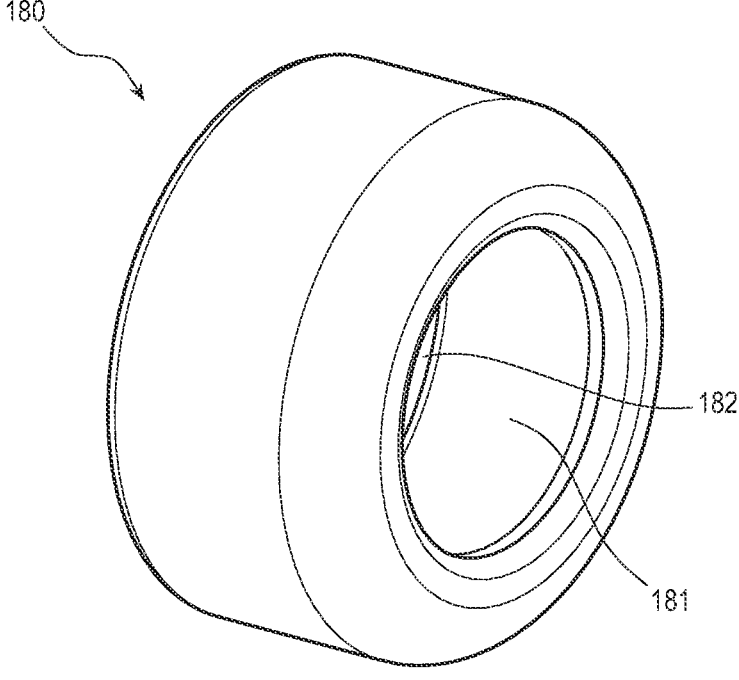
FIG. 7 is a perspective view of an embodiment of a cap cover of the hemostasis valve device of FIG. 1.

In some embodiments, the hemostasis valve device 100 includes a cap cover to provide a technique of identifying an individual hemostasis valve device 100 from other hemostasis valve devices 100 when more than one hemostasis valve device 100 is used in a series. FIG. 7 illustrates an embodiment of a cap cover 180 configured to be disposed over the cap portion 123 of the slide member 120. As illustrated in the depicted embodiment, the cap cover 180 includes a cylindrical shape having a proximal opening 181 and a distal opening 182. The cap cover 180 can be formed of any suitable elastomeric material, such as silicone rubber, thermoplastic elastomer, etc. The cap cover 180 can include a coloring, such as red, blue, or yellow. The coloring can be a pigment or dye mixed into the material of the cap cover 180. In other embodiments, the cap cover 180 may be painted red, blue, or yellow. The cap cover 180 may be applied to the cap portion 123 by inserting the cap portion 123 into the cap cover 180 through the distal opening 182. An inner diameter of the cap cover 180 may be smaller than an outer diameter of the cap portion 123 resulting in stretching of the cap cover 180 as it is applied over the cap portion 123 and retention of the cap cover 180 on the cap portion 123. When applied, the proximal opening 181 aligns with the cap opening 127 to allow passage of medical appliances through the openings 127, 181 into the hemostasis valve device 100.

In some embodiments, as illustrated in FIGS. 8A-10B, the hemostasis valve device 100 can be coupled to a catheter 102 that has been inserted into a patient's vascular system to provide access to treat the patient's brain or other treatment site. During use, the hemostasis valve device 100 can be gripped by the user between a thumb and a finger and actuated a first time to open the valve member 150 to allow passage of a medical appliance (e.g., guidewire) through the hemostasis valve device 100. The hemostasis valve device 100 can be actuated a second time to close the valve member 150 to prevent leakage of blood and/or fluid from the hemostasis valve device 100 and to hold the medical appliance in a desired position relative to the treatment site.

Figure 8A:
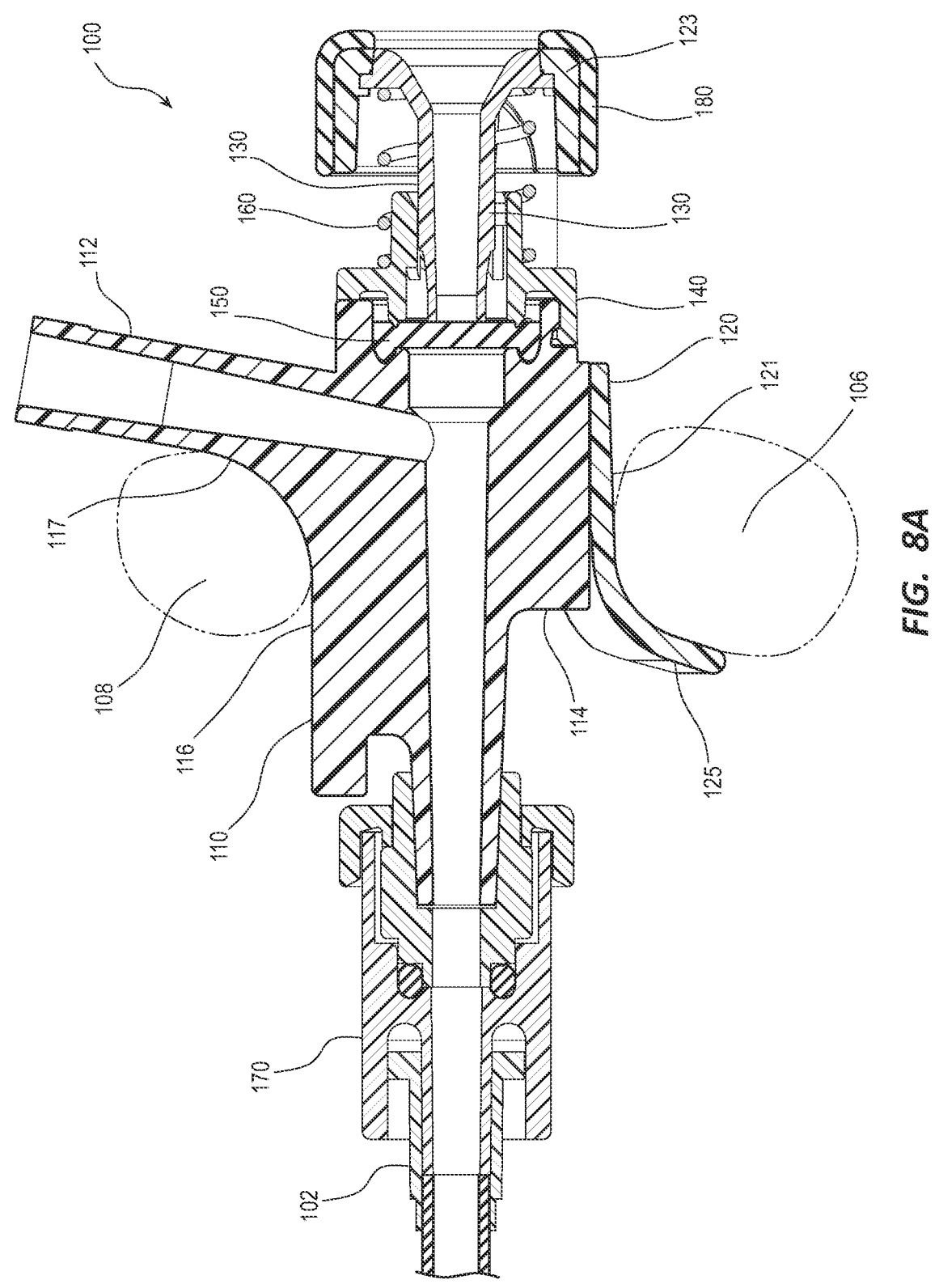
FIG. 8A is a side cross-sectional view of the hemostasis valve device of FIG. 1 in a ready state.
Figure 8B:
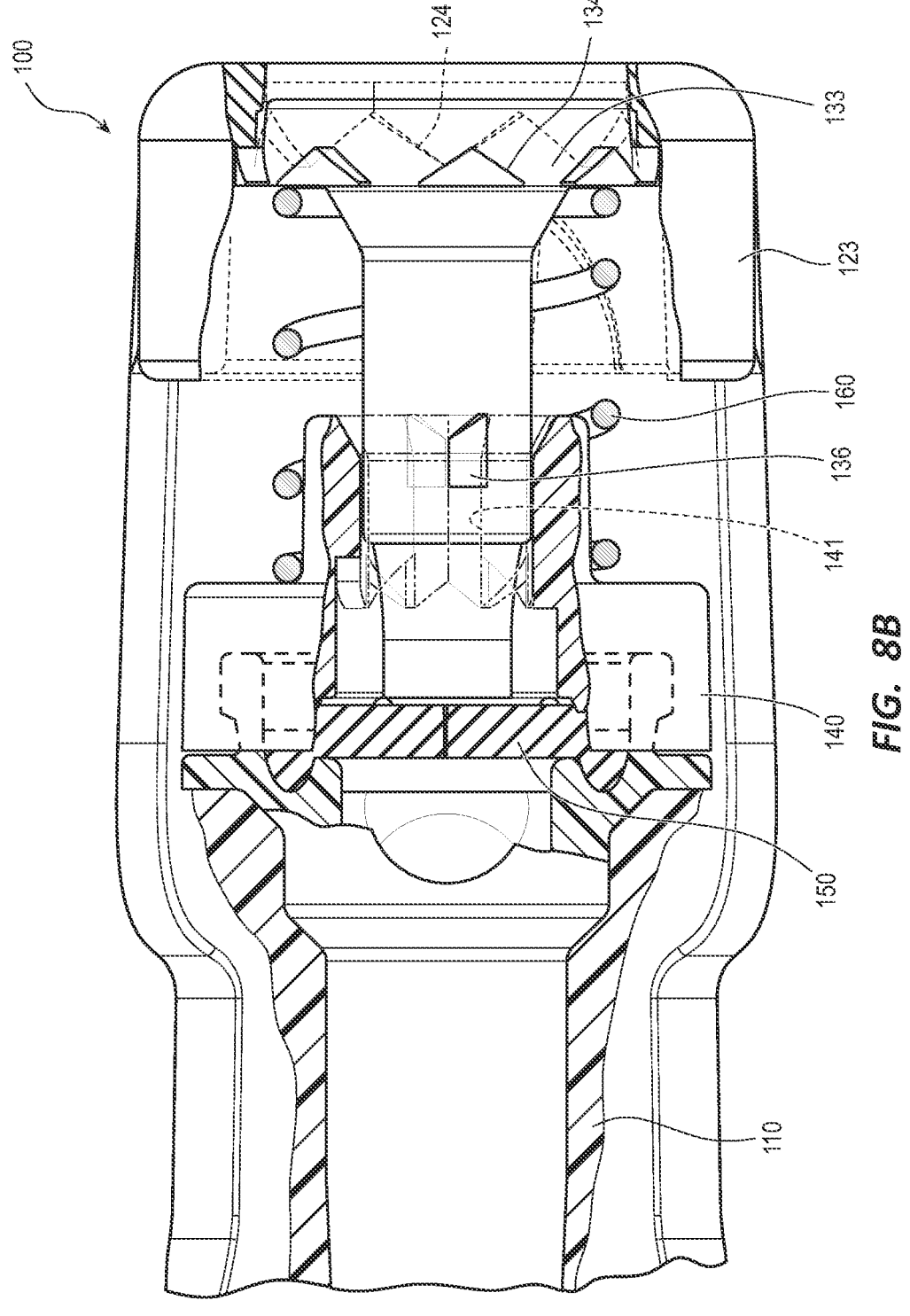
FIG. 8B is a side cross-sectional view of a proximal portion of the hemostasis valve device of FIG. 1 in the ready state.

FIGS. 8A and 8B illustrate the hemostasis valve device 100 is in a ready state. As illustrated in FIG. 8A, the catheter 102 is coupled to the fluid fitting 170. The user's finger 108 is positioned distally of the side-arm 112 on the finger grip portion 113 of the body member 110 and against the finger tab 117. The user's thumb 106 is positioned distally of the valve member 150 on the thumb grip portion 121 of the slide member 120 and against the thumb tab 125. The valve cap 140 is coupled to the body member 110 with the valve member 150 disposed between the body member 110 and the valve cap 140 in a closed state where the slit 152 is closed to prevent blood and/or fluid from passing through the valve member 150. The introducer member 130 is positioned proximally of the valve member 150. The resilient member 160 is positioned between the head portion 133 and the valve cap 140 in a substantially non-compressed state. As further illustrated in FIG. 8B, the guide member 136 is disposed within the guide channel 141. The cap teeth 124 are partially engaging the head teeth 134.

Figure 9A:
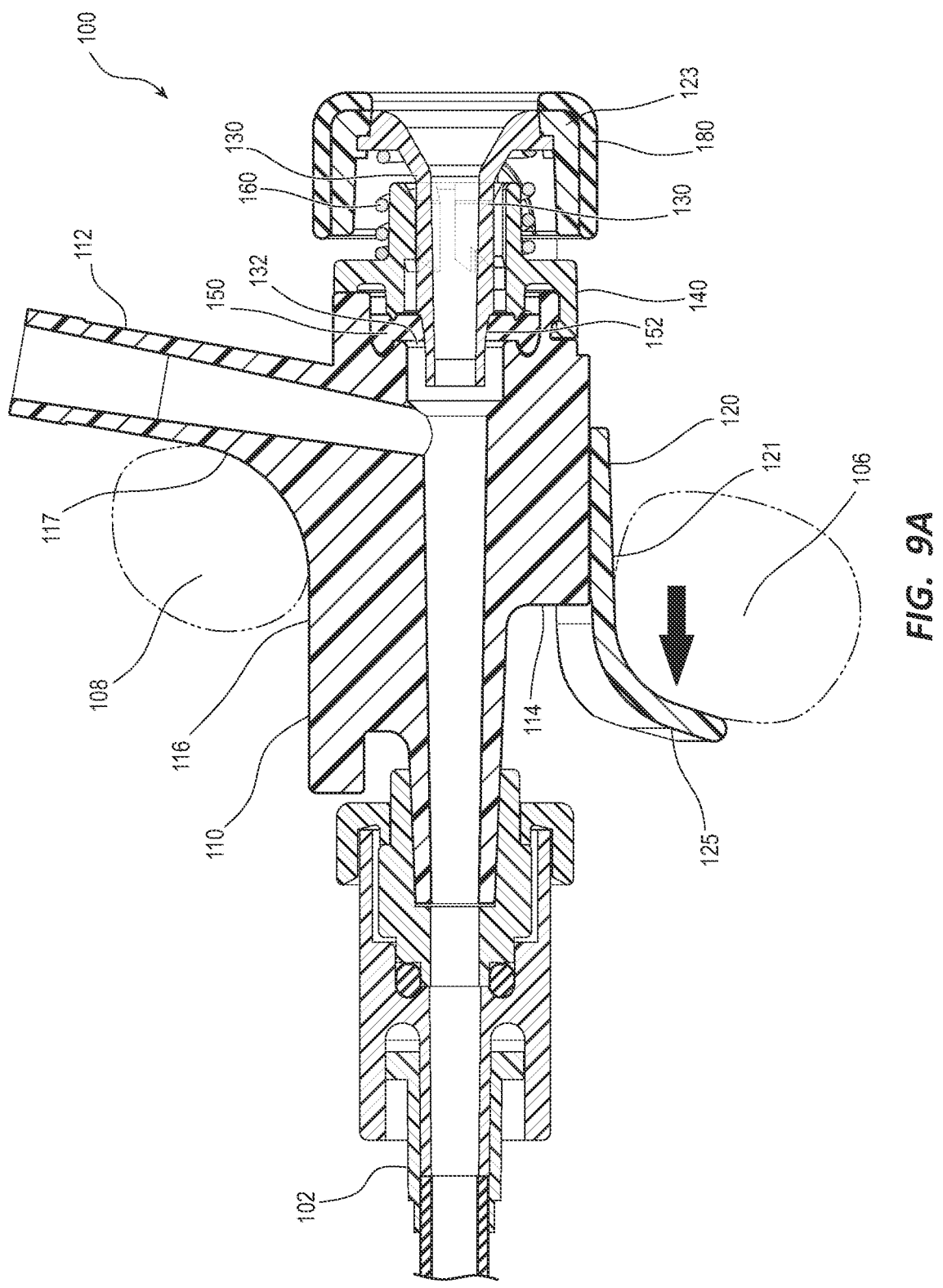
FIG. 9A is a side cross-sectional view of the hemostasis valve device of FIG. 1 in a valve open state.
Figure 9B:
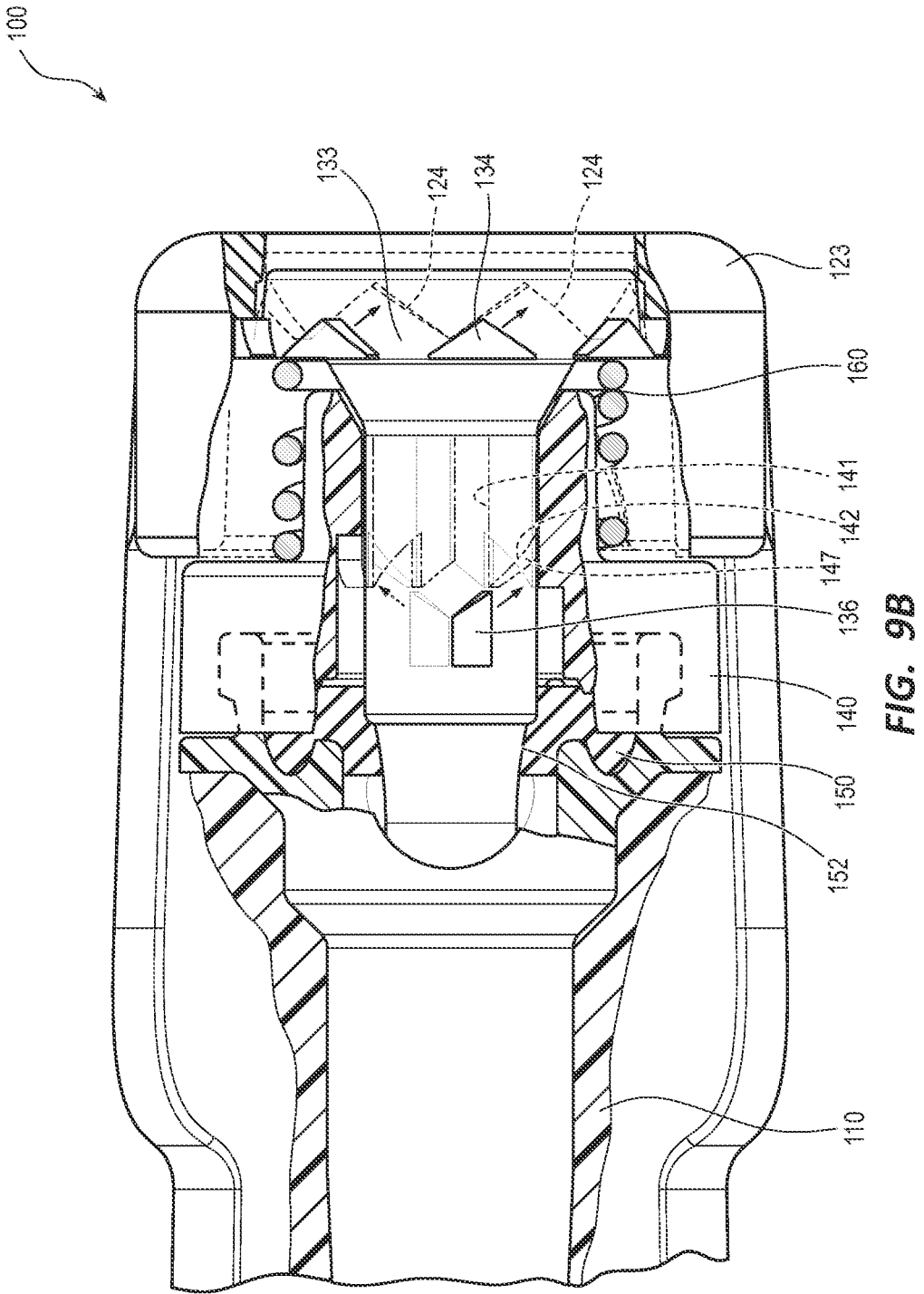
FIG. 9B is a side cross-sectional view of a proximal portion of the hemostasis valve device of FIG. 1 in the valve open state.

FIGS. 9A-9B illustrate the hemostasis valve device 100 transitioned from the ready state to an open state wherein the valve member 150 is opened by the introducer member 130 to allow passage of the medical appliance through the valve member 150. As illustrated in FIG. 9A, the catheter 102 is coupled to the fluid fitting 170. The user's finger 108 is positioned distally of the side-arm 112 on the finger grip portion 113 of the body member 110 and against the finger tab 117 to prevent distal movement of the hemostasis valve device 100. The user's thumb 106 is positioned distally of the valve member 150 on the thumb grip portion 121 of the slide member 120 and against the thumb tab 125 to apply a distally directed force to the thumb tab 125 causing the user's thumb 106 and the slide member 120 to move distally, as indicated by the arrow. The valve cap 140 is coupled to the body member 110 with the valve member 150 disposed between the body member 110 and the valve cap 140. The introducer member 130 is distally displaced from the proximal position to the first distal position by the slide member 120 to push the nose portion 132 through the slit 152 to open the valve member 150. The resilient member 160 is positioned between the head portion 133 and the valve cap 140 in a compressed state, wherein a proximally directed force is applied to the head portion 133. As further illustrated in FIG. 9B, the introducer member 130 is in the first distal position, wherein the guide member 136 is disposed distally of the guide channel 141 allowing the head teeth 134 to slide down an incline of the cap teeth 124, as indicated by the arrows, and the guide member 136 to engage with the proximal surface 147 of the lock member 142 as the resilient member 160 applies the proximally directed force to the head portion 133 causing the introducer member 130 to rotate about a longitudinal axis of the introducer member 130.

Figure 10A:
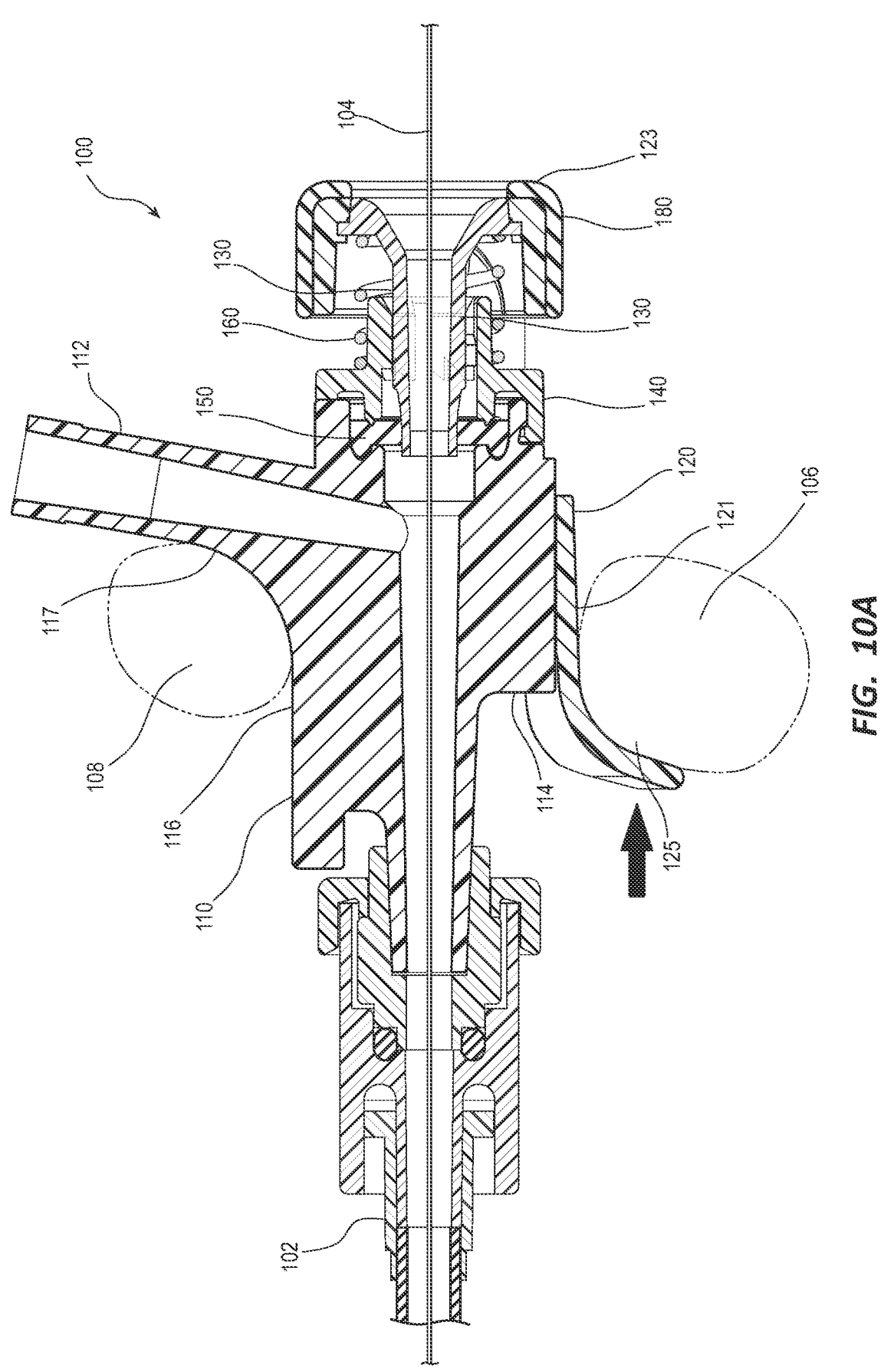
FIG. 10A is a side cross-sectional view of the hemostasis valve device of FIG. 1 in a locked open state.
Figure 10B:
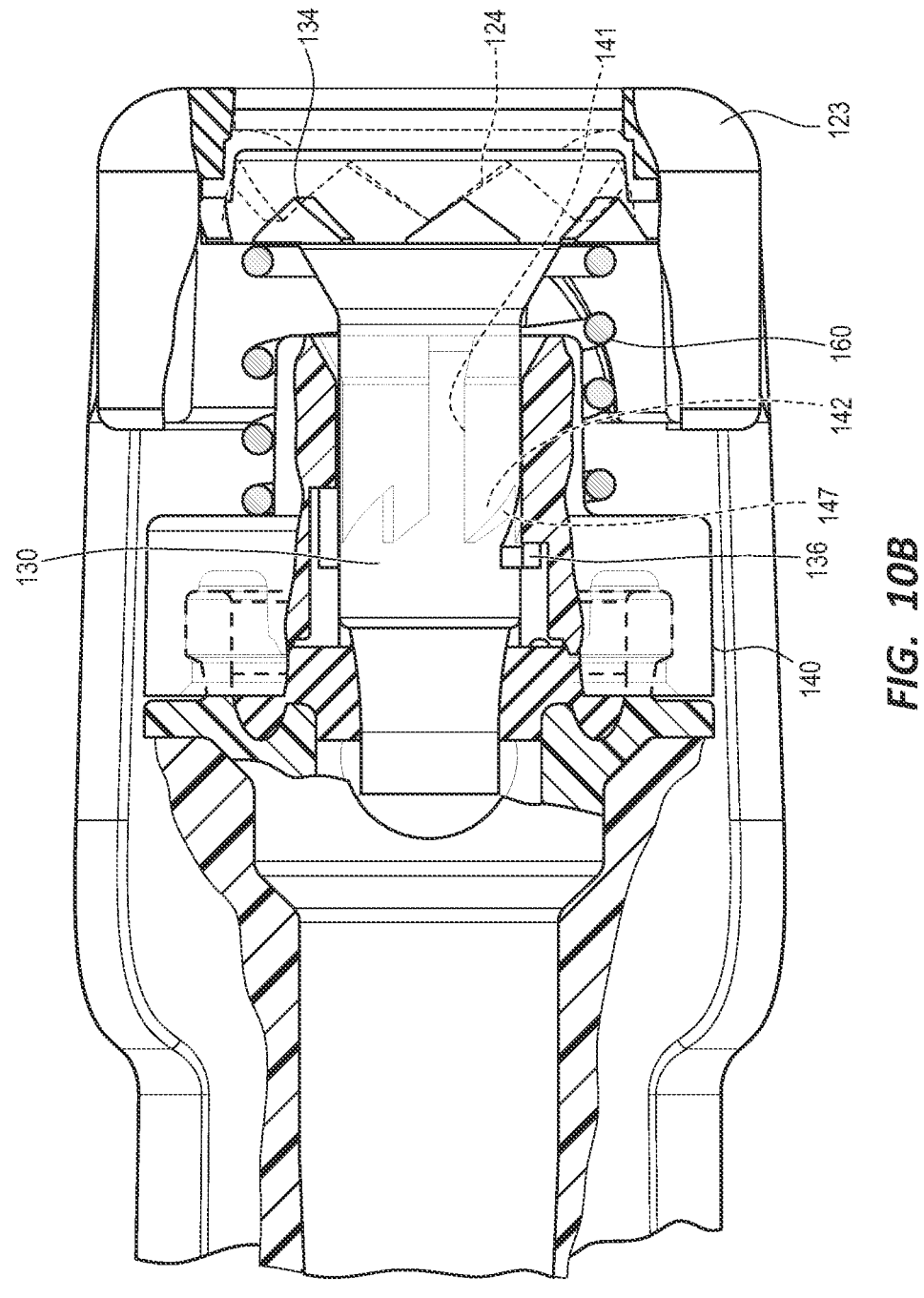
FIG. 10B is a side cross-sectional view of a proximal portion of the hemostasis valve device of FIG. 1 in the locked open state.

FIGS. 10A-10B illustrate the hemostasis valve device 100 transitioned from the open state to a locked open state wherein the valve member 150 is opened by the introducer member 130 to allow passage of the medical appliance 104 through the valve member 150 and the introducer member 130 is locked in the second distal position. As illustrated in FIG. 10A, the catheter 102 is coupled to the fluid fitting 170. The user's finger 108 is positioned distally of the side-arm 112 on the finger grip portion 113 of the body member 110 and against the finger tab 117. The user's thumb 106 is positioned distally of the valve member 150 on the thumb grip portion 121 of the slide member 120 and against the thumb tab 125 to release the distally directed force to the thumb tab 125 causing the patient's thumb 106 and the slide member 120 to move proximally, as indicated by the arrow. The valve cap 140 is coupled to the body member 110 with the valve member 150 disposed between the body member 110 and the valve cap 140. The introducer member 130 is proximally displaced to the second distal position by a proximally directed force applied to the head portion 133 by the resilient member 160 to lock the hemostasis valve device 100 in the locked open state. The resilient member 160 is positioned between the head portion 133 and the valve cap 140 in a semi-compressed state, wherein the proximally directed force is applied to the head portion 133. As further illustrated in FIG. 10B, the introducer member 130 is in the second distal position. The introducer member 130 is rotated about a longitudinal axis of the introducer member 130, wherein the head teeth 134 are partially engaged with the cap teeth 124 and the guide member 136 is fully engaged with the proximal surface 147 of the lock member 142 to lock the introducer member 130 in the second distal position that is proximal of the first distal position and lock the hemostasis valve device 100 in the locked open state.

Figure 11A:
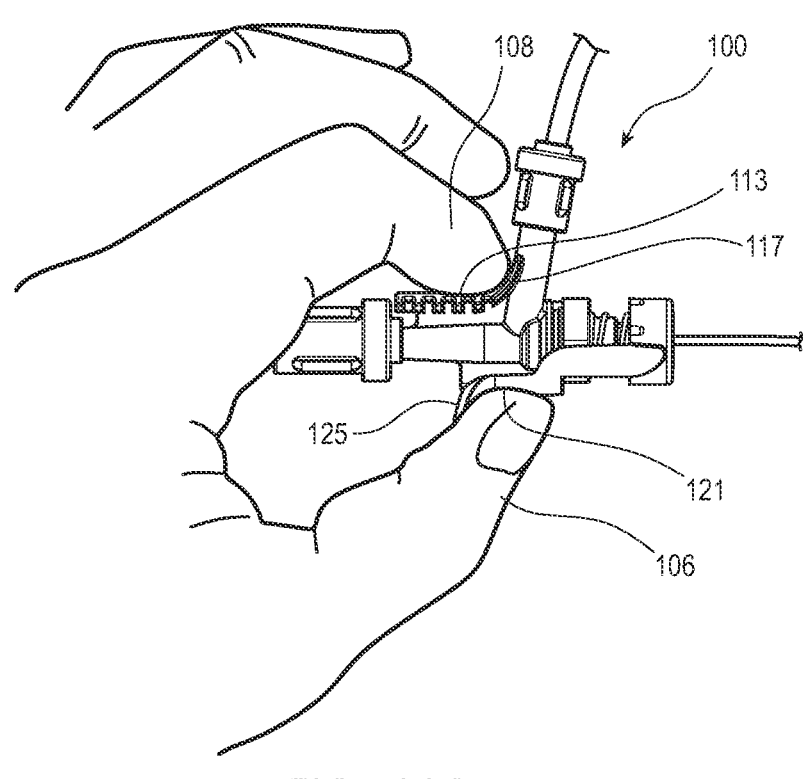
FIG. 11A is a top view of the hemostasis valve device of FIG. 1 in a ready state being gripped by a user's overhand grip.
Figure 11B:
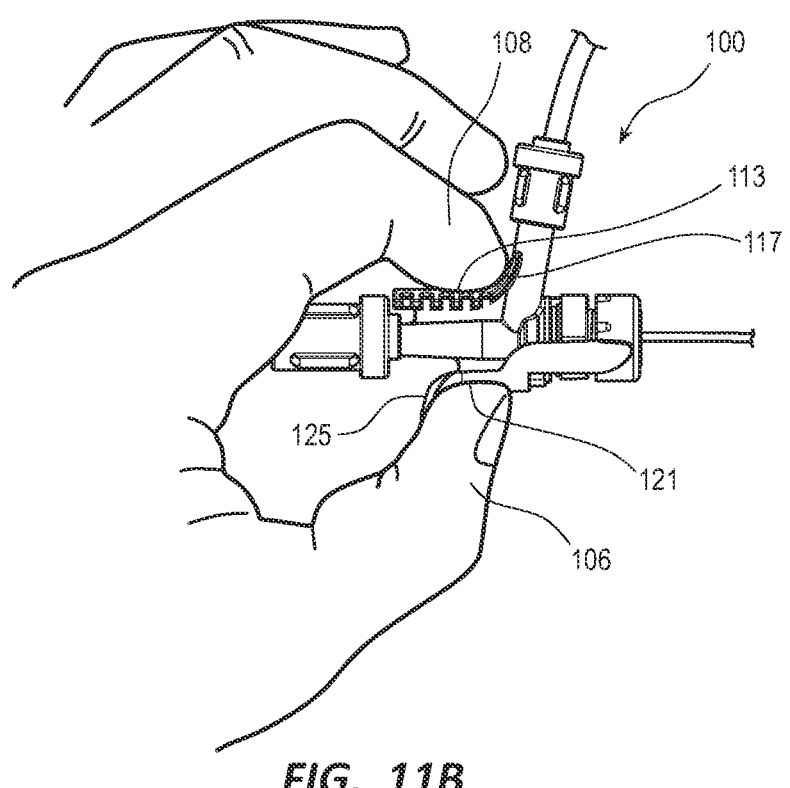
FIG. 11B is a top view of the hemostasis valve device of FIG. 1 in a valve open state being gripped by a user's overhand grip.

FIGS. 11A and 11B illustrate a method of handling the hemostasis valve device 100 during use. As illustrated in FIG. 11A, the user can grip the hemostasis valve device 100 in an overhand grip between a thumb and a finger (e.g., a first finger) in a ready state. The thumb can be placed on the thumb grip portion 121 with the thumb resting against the thumb tab 125. The finger can be placed opposite the thumb on the finger grip portion 113 with the finger resting against the finger tab 117. In the overhand grip, the hemostasis valve device 100 can be visible between the thumb and finger allowing the user to visualize fluid and/or medical appliances passing through the hemostasis valve device 100.

As illustrated in FIG. 11B, when the hemostasis valve device 100 is actuated, the thumb applies a distally directed force to the thumb tab 125 to distally displace the slide member 120 to open the valve member 150 with the introducer member 130. When the thumb is moved distally, the finger can apply a proximally directed force to the finger tab 117 to prevent the hemostasis valve device 100 from being displaced distally. In some embodiments, a second finger can be placed on the fluid fitting 170 to prevent pivoting of the hemostasis valve device 100 about a pivot point between the finger and the thumb. In other words, the second finger can apply a force to the fluid fitting 170 opposite and at least equal to the rotational force about the pivot point to prevent rotation of the hemostasis valve device 100 about the pivot point. Rotation of the hemostasis valve device 100 may cause rotation of a distal end of the catheter coupled to the hemostasis valve device 100 and/or medical appliance passing through the hemostasis valve device 100 relative to the area of treatment.

In some embodiments, the overhand grip may allow the user to actuate the hemostasis valve device 100 and pass medical appliances through the hemostasis valve device 100 without releasing the overhand grip.

FIG. 12 depicts an embodiment of a hemostasis valve device 200 that resembles the hemostasis valve device 100 described above in certain respects. Accordingly, like features are designated with like reference numerals, with the leading digit incremented to "2." For example, the embodiment depicted in FIG. 12 includes a body member 210 that may, in some respects, resemble the body member 110 of FIG. 1. Relevant disclosure set forth above regarding similarly identified features thus may not be repeated hereafter. Moreover, specific features of the body member 110 and related components shown in FIGS. 1-11B may not be shown or identified by a reference numeral in the drawing or specifically discussed in the written description that follows. However, such features may clearly be the same, or substantially the same, as features depicted in other embodiments and/or described with respect to such embodiments. Accordingly, the relevant descriptions of such features apply equally to the features of the hemostasis valve device 200 and related components depicted in FIG. 12. Any suitable combination of the features, and variations of the same, described with respect to the hemostasis valve device 100 and related components illustrated in FIGS. 1-11B can be employed with the hemostasis valve device 200 and related components of FIG. 12, and vice versa.

As illustrated in FIG. 12, the hemostasis valve device 200 includes a body member 210 and a slide member 220. The body member 210 includes a rail 214 that includes a radial inwardly incline. The incline can be angled at angle a that ranges from about two degrees to about ten degrees and may be about six degrees. A thumb grip portion 221 of the slide member 220 is slidingly coupled to the rail 214. When the slide member 220 is distally displaced by a user's thumb against the thumb tab 225, the thumb grip portion 221 is displaced toward a longitudinal axis of the hemostasis valve device 200 to prevent rotation of the hemostasis valve device 200 about a pivot point disposed between the user's thumb and finger.

FIGS. 13A and 13B illustrate another embodiment of a hemostasis valve device 300. As depicted in the illustrated embodiment, the hemostasis valve device 300 includes a body member 310, a slide member 320, a valve cap 340, a valve member 350 having a slit 352 therethrough, and a resilient member 360. The slide member 320 includes a thumb grip portion 321, a cap portion 323, and a thumb tab 325. An introducer portion 329 extends distally from the cap portion 323. The introducer portion 329 is cylindrical in shape and includes a bore extending therethrough. The introducer portion 329 has a tapered nose portion 332 disposed a distal end. The resilient member 360 is depicted as a compression spring disposed between the valve cap 340 and the cap portion 323.

FIG. 13A depicts the hemostasis valve device 300 in a ready state wherein the slide member 320 is in a proximal position such that the introducer portion 329 is positioned proximal to the valve member 350. The resilient member 360 is in a substantially non-compressed state. FIG. 13B depicts the hemostasis valve device 300 in a valve open state wherein the slide member 320 is displaced distally, as indicated by the arrow, for example, by a user's thumb and the resilient member 360 is substantially compressed. The nose portion 332 is disposed through the slit 351 to provide an open passage through the introducer portion 329 into a bore of the body member 310. Upon release of the user's thumb from the thumb tab 325, the resilient member 360 can apply a proximally directed force to the cap portion 323 to displace the slide member 320 proximally resulting in proximal displacement of the introducer portion 329 and closure of the slit 352.

FIGS. 14A and 14B illustrate another embodiment of a hemostasis valve device 400. As depicted in the illustrated embodiment, the hemostasis valve device 300 includes a body member 410, a slide member 420, a valve cap 440, and a valve member 450 having a slit 452 therethrough. The slide member 420 includes a thumb grip portion 421, a cap portion 423, and a thumb tab 425. An introducer portion 429 extends distally from the cap portion 423. The introducer portion 429 is cylindrical in shape and includes a bore extending therethrough. The introducer portion 429 has a tapered nose portion 432 disposed adjacent a distal end.

FIG. 14A depicts the hemostasis valve device 400 in a ready state wherein the slide member 420 is in a proximal position such that the introducer portion 429 is positioned proximal to the valve member 450. FIG. 14B depicts the hemostasis valve device 400 in a valve open state wherein the slide member 420 is displaced distally, as indicated by the arrow, for example, by a user's thumb. The nose portion 432 is disposed through the slit 451 to provide an open passage through the introducer portion 429 into a bore of the body member 410. Upon release of the user's thumb from the thumb tab 425, the slit 452 can provide a proximally directed force to the nose portion 432 to displace the slide member 420 proximally resulting in proximal displacement of the introducer portion 429 and closure of the slit 452. In some embodiments, a lubricating material, such as silicone oil, may be applied to the nose portion 432 to facilitate proximal displacement of the introducer portion 429.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of opening a hemostasis valve may include one or more of the following steps: positioning a user's finger of a user's first hand on a finger grip of a hemostasis valve device; positioning a user's thumb of the user's first hand on an actuator circumferentially opposite of the finger grip, wherein the user's thumb is located distal of the hemostasis valve; distally displacing the actuator with the user's thumb a first time while the user's finger remains stationary; distally displacing an introducer member from a proximal position to a first distal position by the actuator through the hem ostasis valve; releasing the actuator; and locking the introducer member in a second distal position through the hemostasis valve. Other steps are also contemplated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

In the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest to the practitioner during use. As specifically applied to a hemostasis valve device of this disclosure, the proximal end of the device refers to the end nearest to the cap and the distal end refers to the opposite end, the end nearest the fluid fitting.

"Fluid" is used in its broadest sense, to refer to any fluid, including both liquids and gases as well as solutions, compounds, suspensions, etc., that generally behave as fluids.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially non-compressed" is recited with respect to a feature, it is understood that in further embodiments, the feature can have a precisely non-compressed configuration.

The terms "a" and "an" can be described as one, but not limited to one. For example, although the disclosure may recite a body member having "a side-arm," the disclosure also contemplates that the body member can have two or more side-arms.

Unless otherwise stated, all ranges include both endpoints and all numbers between the endpoints.

Recitation in the claims of the term "first" with respect to a feature or element does not necessarily imply the existence of a second or additional such feature or element.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A hemostasis valve device, comprising:
a body member comprising:
    a body bore extending therethrough;
    a side-arm comprising a side-arm bore in communication with the body bore;
    a finger grip portion configured to be gripped by a finger of a user; and
    a guide rail extending along an exterior surface of the body member and aligned with a longitudinal axis of the body member;
a slide member coupleable to the body member comprising:
    a thumb grip portion comprising a thumb tab, the thumb grip extending from the slide member to a distal end, the thumb grip extending radially outward from a longitudinal axis of the slide member such that the distal end is disposed radially outward from the slide member;
    a guide slot disposed in an interior surface of the slide member and aligned with the longitudinal axis of the slide member, wherein the slot is configured to slidingly receive the rail;
    a cap portion disposed at a proximal end of the slide member and comprising internal, distally directed cap teeth;
an introducer member comprising:
    an introducer bore passing therethrough;
    a nose portion disposed at a distal end;
    a head portion disposed at a proximal end and comprising external, proximally directed head teeth configured to operably engage with the internal, distally directed teeth when the hemostasis valve device is in an actuating state; and
    a body portion extending between the nose portion and the head portion and comprising a guide member extending radially outward from an exterior surface;
a valve cap fixedly coupled to the body member, comprising:
    an internal guide channel slidingly coupleable with the guide member when the hemostasis valve device is in the actuating state; and
    an internal lock member coupleable with the guide member when the hemostasis valve device is in a locked open state;
a valve member disposed between the body member and the valve cap and penetrable by the nose portion; and
a resilient member disposed between the valve cap and the head portion.

2. The hemostasis valve device of claim 1.
wherein the finger grip portion is disposed distally of and coupled to the side-arm; and
wherein the finger grip portion comprises an arcuate shape.

3. The hemostasis valve of claim 1, wherein the thumb tab is disposed distally of the valve.

4. The hemostasis valve device of claim 1, wherein the thumb tab is disposed circumferentially 180 degrees from the finger grip portion to allow the user to grip the hemostasis valve device between a thumb and a finger.

5. The hemostasis valve device of claim 1, wherein the thumb tab is configured to be engaged by a thumb of the user to longitudinally displace the slide member relative to the body.

6. The hemostasis valve device of claim 1, wherein the nose portion is configured to penetrate through the valve member when the introducer member is distally displaced by the slide member.

7. The hemostasis valve device claim 1, wherein the introducer member is rotatable about a longitudinal axis of the hemostasis valve device.

8. The hemostasis valve device of claim 1, wherein the introducer member is distally displaceable by the slide member when the hemostasis valve device is in the actuating state.

9. The hemostasis valve device of claim 1, wherein the introducer member is prevented from proximal movement when the hemostasis valve device is in the locked open state.

10. The hemostasis valve device of claim 1, wherein the nose portion is disposed through the valve member when the hemostasis valve device is in the locked open state.

11. The hemostasis valve device of claim 1, further comprising a fluid fitting coupled to a distal end of the body member and in fluid communication with the body bore.

12. The hemostasis valve of claim 1, wherein the thumb tab is disposed distal of a proximal portion of the finger grip portion.

13. The hemostasis valve of claim 1, wherein a portion of the thumb tab extends radially outward at a right angle relative to the longitudinal axis of the slide member.

14. The hemostasis valve of claim 1, wherein the thumb tab comprises a concave arcuate surface.

15. A hemostasis valve device, comprising:
a body member comprising:
    a body bore extending therethrough;
    a side-arm comprising a side-arm bore in communication with the body bore;
    a finger grip portion configured to be gripped by a finger of a user; and
    a guide rail extending along an exterior surface of the body member and aligned with a longitudinal axis of the body member;

a slide member coupleable to the body member comprising:
    a thumb grip portion comprising a thumb tab disposed at a distal end of the thumb grip portion, the thumb grip extending radially outward from a longitudinal axis of the slide member such that the thumb tab is disposed radially outward from the slide member;
    a guide slot disposed in an interior surface of the slide member and aligned with the longitudinal axis of the slide member, wherein the slot is configured to slidingly receive the rail;
    a cap portion disposed at a proximal end of the slide member; and
    an introducer portion extending distally from the cap portion comprising:
        an introducer bore passing therethrough;
        a nose portion disposed at a distal end; and
a valve cap fixedly coupled to the body member, comprising:
    a valve member disposed between the body member and the valve cap and penetrable by the nose portion.

16. The hemostasis valve device of claim 15, wherein the thumb grip portion extends parallel to the longitudinal axis of the slide member.

17. The hemostasis valve device of claim 15,
wherein the finger grip portion is disposed distally of and coupled to the side-arm; and
wherein the finger grip portion comprises an arcuate shape.

18. The hemostasis valve of claim 15, wherein the thumb tab is disposed distally of the valve.

19. The hemostasis valve device of claim 15, wherein the thumb tab is disposed circumferentially 180 degrees from the finger grip portion to allow the user to grip the hemostasis valve device between a thumb and a finger.

20. The hemostasis valve device of claim 1, wherein the thumb tab is configured to be engaged by a thumb of the user to longitudinally displace the slide member relative to the body.

* * * * *